US008808732B2

(12) United States Patent
Dong

(10) Patent No.: US 8,808,732 B2
(45) Date of Patent: Aug. 19, 2014

(54) FILM FORMING PERSONAL CARE COMPOSITIONS AND METHODS

(75) Inventor: Shaosheng Dong, Campbell, CA (US)

(73) Assignee: Shaosheng Dong, Campbell, CA (US)

( * ) Notice: Subject to any disclaimer, the term of this patent is extended or adjusted under 35 U.S.C. 154(b) by 0 days.

(21) Appl. No.: 13/696,726

(22) PCT Filed: May 9, 2011

(86) PCT No.: PCT/US2011/035785
§ 371 (c)(1),
(2), (4) Date: Nov. 7, 2012

(87) PCT Pub. No.: WO2011/143131
PCT Pub. Date: Nov. 17, 2011

(65) Prior Publication Data
US 2013/0058880 A1 Mar. 7, 2013

Related U.S. Application Data

(60) Provisional application No. 61/333,750, filed on May 11, 2010.

(51) Int. Cl.
*A61F 13/00* (2006.01)
*A61K 9/70* (2006.01)
*C08K 5/5419* (2006.01)
*C08K 5/5435* (2006.01)
*C08G 77/26* (2006.01)
*C08G 77/14* (2006.01)

(52) U.S. Cl.
CPC .............. *C08K 5/5435* (2013.01); *C08G 77/26* (2013.01); *C08G 77/14* (2013.01); *C08K 5/5419* (2013.01)

USPC .......................................... 424/449; 424/443

(58) Field of Classification Search
None
See application file for complete search history.

(56) References Cited

U.S. PATENT DOCUMENTS

| 2,506,320 | A |   | 5/1950 | Vail |   |
|---|---|---|---|---|---|
| 2003/0044611 | A1 | * | 3/2003 | Stark et al. | 428/405 |
| 2005/0268405 | A1 |   | 12/2005 | Brun et al. |   |
| 2006/0110415 | A1 | * | 5/2006 | Gupta | 424/401 |
| 2006/0199020 | A1 |   | 9/2006 | Stark |   |
| 2007/0014756 | A1 |   | 1/2007 | Touchot |   |
| 2010/0233146 | A1 | * | 9/2010 | McDaniel | 424/94.2 |

OTHER PUBLICATIONS

International Search Report (ISA/US) for International Application No. PCT/US2011/035785, mailed Jul. 19, 2011, 3 pages.

* cited by examiner

Primary Examiner — Susan Tran

(57) ABSTRACT

Compositions, kits and methods of preparing a biocompatible film for cosmetic or medical uses are disclosed. The compositions or kits contain polyvinyl acetal (PVA), siloxane and a solvent. The siloxane can have a hydrophilic group. Once the solvent content is reduced, for instance, by evaporation, the mixture of PVA and siloxane is solidified, forming a film. The compositions and kits, optionally, further include one or more of an antimicrobial agent, a pigment, an anti-inflammatory agent, an anesthetic agent or a hemostatic agent. Such a film can be used, for example, in the form of an antimicrobial sealant, a liquid bandage, body paints, scar camouflage, water-proof sun block, makeup sealer, or antimicrobial wipe or spray.

43 Claims, No Drawings

FILM FORMING PERSONAL CARE COMPOSITIONS AND METHODS

CROSS-REFERENCE TO RELATED APPLICATIONS

This application is a national stage application under 35 U.S.C. §371 of International Application No. PCT/US2011/035785, filed May 9, 2011, which in turn claims the benefit under 35 U.S.C. §119(e) to U.S. Provisional Application No. 61/333,750, filed May 11, 2010, the content of which is hereby incorporated by reference in its entirety into the present disclosure.

FIELD OF THE DISCLOSURE

The present disclosure relates generally to compositions and methods for cosmetic, medical and personal care.

BACKGROUND

Throughout the disclosure, various technical and patent literature are identified by a bibliographic citation. The contents of all technical and patent literature are incorporated into the present disclosure by reference in their entirety.

Film forming materials have broad use in therapeutic, cosmetic and personal care applications. Such materials are used to coat a body surface, such as skin, nail and hair, for the protection of the surface or to apply therapeutic or cosmetic ingredients to the surface.

The film forming process typically involves a chemical reaction and solvent evaporation. The chemical reaction, such as polymerization of cyanoacrylate, can be quickly initiated by water or keratinous protein and forms a polymeric film on a surface. Alternatively, the chemical reaction may be epoxy-curing, UV or thermal polymerization of unsaturated monomers, radiation-induced curing or other ring-opening reactions.

Solvent evaporation, on the other hand, can help form a uniform layer of film on the surface. Water is widely used as a non-toxic solvent or as a dispersing medium as in the cases for latex and dispersions. Alcoholic solvents are another group of solvents, although many film forming materials have limited or no solubility in these solvents. Other examples of organic solvents include alkyl acetate, acetone and toluene.

Many film forming materials rely solely on the physical interactions between the material and the body surface to adhere to the surface. These interactions include van de Waals forces, dipolar interaction and hydrogen bonding. In general, these interactions are relatively weak, which often leads to poor adhesion to the skin and premature flake-off of the resultant film. Moreover, grease and sweat on the skin, for example, can further weaken the adhesion.

There has been a long felt need for improved film forming compositions, which are simple to apply, can form a flexible film quickly and adhere strongly to a substrate. It is also preferred that the formed films are breathable and non-toxic.

SUMMARY

It is herein discovered, unexpectedly, that when polyvinyl acetal (PVA) is mixed with siloxane having a hydrophilic group, in a solvent, it constitutes a film forming composition suitable for medical and cosmetic uses. Thus, the present disclosure provides compositions, kits and methods of preparing a biocompatible film for cosmetic or medical uses. The compositions or kits contain polyvinyl acetal (PVA), siloxane and a solvent. Once the solvent content is reduced, for instance, by evaporation, the mixture of PVA and siloxane is solidified, forming a film. The compositions and kits, optionally, further include one or more of an antimicrobial agent, a pigment, an anti-inflammatory agent, an anesthetic agent or a hemostatic agent.

Polyvinyl acetals have been used in the production of safety glass in automotive construction and for architectural uses. Plasticized polyvinyl butyral films, for example, are used as an intermediate layer in glazing units.

For applications on human surface, however, PVA are not flexible enough and do not provide adequate adhesion to the surface. The inadequate adhesion is caused, in part, by the inherit brittleness of PVA. Thus, plasticizers and adhesion promoters are sometimes added to PVA to provide better adhesion. Such plasticizers and adhesion promoters, however, are either not suitable for human use. For example, certain such films show coloration due to yellowing of aminosilanes and their unpleasant odor and skin-irritant action, a known problem when using amino-functional compounds. When plasticizers are used to make the film flexible, it inevitably weakens adhesion between the film and skin, due to the lack of strong interactions with skin.

The present discovery, however, shows that the combination of PVA and siloxane, in particular siloxane having a hydrophilic group, or alternatively a functional or a polar group, makes the composition not only adequately adhesive to a body surface, but also provides good flexibility and breathability, an obvious advantage for human use.

It is further discovered that such compositions can also include therapeutic or cosmetic ingredients, enabling a broad range of applications in personal care. Such compositions can form a film that can be used, for example, in the form of an antimicrobial sealant, a liquid bandage, body paints, scar camouflage, water-proof sun block, makeup sealer, or antimicrobial wipe or spray.

Accordingly, the present disclosure provides, in one embodiment, a composition comprising polyvinyl acetal (PVA) and siloxane, wherein the siloxane comprises a hydrophilic group. Alternatively, the siloxane comprises a functional group or a polar group. In some aspects, the composition further comprises a solvent.

In one aspect, the hydrophilic group comprises one or more of the group of a halogen, oxygen, nitrogen, sulfur or phosphorus. In another aspect, the hydrophilic group is one or more of the group of a carboxylic acid, an amino group, a hydroxyl group, an epoxy group or an anhydride group.

Examples of the hydrophilic group include, without limitation,
(3-glycidoxypropyl)dimethylethoxysilane,
(3-glycidoxypropyl)pentamethyldisiloxane,
(3-glycidoxypropyl)methyldiethoxysilane,
(3-glycidoxypropyl)triethoxysilane,
5,6-epoxyhexyltriethoxysilane,
(3-glycidoxypropyl)bis(trimethylsiloxy)methylsilane,
1,3-bis(glycidoxypropyl)tetramethyldisiloxane,
1,5-bis(glycidoxypropyl)-3-phenyl-1,1,3,5,5-pentamethyltrisiloxane,
bis[2-(3,4-epoxycyclohexyl)ethyl]tetramethyldisiloxane,
mono-(2,3-epoxy)propylether terminated polydimethylsiloxane,
epoxypropoxypropyl terminated polydimethylsiloxane,
epoxycyclohexylethyl terminated polydimethylsiloxane,
epoxypropylheptaisobutyl-T8-silsesquioxane,
succinic anhydride terminated polydimethylsiloxane,
bis(2-hydroxyethyl)-3-aminopropyltriethoxysilane,
1,3-bis(hydroxypropyl)tetramethyldisiloxane, 1,3-bis(hydroxybutyl)tetramethyldisiloxane,
monocarbinol terminated polydimethylsiloxane,
3-[hydroxy(polyethyleneoxy)propyl]heptamethyltrisiloxane,
trimethylsilylpropionic acid,
1,3-bis(3-carboxypropyl)tetramethyldisiloxane, or
3-(triethoxysilyl)propylsuccinic anhydride.

In some aspects, the siloxane has a structure of:

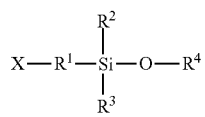

wherein:
X is selected from the group consisting of an amino group, an epoxy group, a hydroxyl group, a carboxylic acid group, and a maleic anhydride group;
$R^1$ is a divalent organic group optionally substituted with an oxygen, nitrogen, or sulfur atom, or is selected from the group consisting of a substituted or non-substituted $C_2$-$C_{20}$-aliphatic group, a substituted or non-substituted aromatic group, and a substituted or non-substituted aliphatic aromatic group;
$R^2$ and $R^3$ are independently selected from the group consisting of a lower alkyl group, a lower alkoxy group, and a polymeric siloxane group;
$R^4$ is selected from the group consisting of a lower alkyl group, an oligomeric or a polymeric siloxane group and

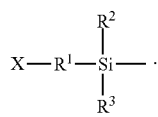

In one aspect, the PVA has a molecular weight from about 25,000 to about 250,000, or alternatively from about 50,000 to about 200,000, or alternatively from about 75,000 to about 175000, or alternatively from about 100,000 to about 150,000.

In another aspect, the PVA has a degree of polymerization of from about 200 to about 2,000, or alternatively from about 300 to about 1500, or alternatively from about 400 to about 1200, or alternatively from about 400 to about 800.

In some aspects, the PVA has a degree of hydrolysis greater than about 70 mol %, or alternatively about 80 mol %, or about 85 mol %, or about 90 mo %, or about 95 mol %, or about 98 mol %, or about 99 mol %.

In still some aspects, the PVA has a structure of:

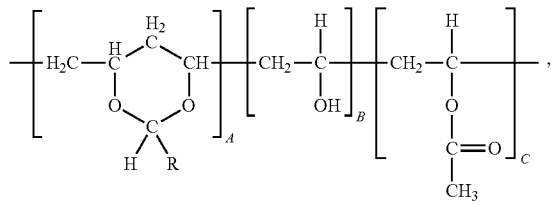

wherein R is selected from the group of methyl, ethyl, propyl, butyl, hexyl or benzyl, A is an integer in the range of from about 50 to about 1800, B is an integer in the range of from about 10 to about 800 and C is an integer from the range of from about 0 to about 1000.

In a particular aspect, the PVA comprises polyvinyl butyral (PVB). In one embodiment, the PVB constitutes about 70% to about 90% by weight of the PVA.

Still in another aspect, the PVA has a concentration of from about 0.1 wt/vol % to about 60 wt/vol % in the composition, or alternatively from about 1 wt/vol % to about 30 wt/vol % in the composition, or alternatively from about 2 wt/vol % to about 25 wt/vol % in the composition, or alternatively from about 5 wt/vol % to about 20 wt/vol % in the composition, or alternatively from about 10 wt/vol % to about 15 wt/vol % in the composition.

The solvent in the composition can be an inorganic solvent or an organic solvent. Non-limiting examples of inorganic solvent include water, saline or combinations thereof. Non-limiting examples of organic solvent includes one or more of the group of methanol, ethanol, isopropanol, n-propanol, butanol, methyl cellosolve, butyl cellosolve, methyl acetate, ethyl acetate, isopropyl acetate, butyl acetate, acetone, methyl ethyl ketone, toluene, xylene, dichloromethane or chloroform.

In another embodiment, the composition further comprises an antimicrobial agent. The antimicrobial agent can be one or more of the group of silver compounds, quaternary ammonium cations, or acid-anionic surfactants.

In yet another embodiment, the composition further comprises a pigment, such as, but not limited to, iron oxides, titanium dioxides, extender pigments ultramarine pigments, manganese violet, mixed metal oxide pigments, fluorescent pigments, carbon black, magnetite, lodestone, or magnetic iron oxide.

Still in another embodiment, the composition further comprises an anti-inflammatory agent. Examples of anti-inflammatory agent include, without limitation, ibuprofen, naproxen sodium, aspirin, ketoprofen, procaine, cocaine, lidocaine, prilocaine, bupivacaine, levobupivacaine, ropivacaine or dibucaine.

Yet another embodiment provides a composition that further comprises an anesthetic agent. In one aspect, the anesthetic agent is one or more of the group of lidocaine, prilocaine, bupivicaine, levobupivacaine, ropivacaine, mepivacaine or dibucaine.

Also provided, in still another embodiment, is a composition further comprising a hemostatic agent. In some aspects, the hemostatic agent is one or more of the group of oxidized regenerated cellulose, gelatin, fibrin, thrombin, alginate, zeolite, collagen or chitosan.

The composition of any of the above embodiment can be provided in a solid, gel or liquid form, can be prepared in a form that is pharmaceutically acceptable.

In one embodiment, the present disclosure provides a composition prepared by admixing PVA and siloxane in a solvent, wherein the siloxane comprises a hydrophilic group. Examples of PVA, siloxane, solvent and hydrophilic group are provided above and generally in the disclosure.

Also provided, in one embodiment, is a film that is obtained by reducing the content of the solvent in a composition of any of the above embodiments, or a film that is obtainable by reducing the content of the solvent in a composition of any of the above embodiments. In one aspect, the solvent is reduced by evaporation.

Kits are also provided, comprising, in two or more separate compartments, polyvinyl acetal (PVA), siloxane and a solvent. In some aspects, the kit further comprises one or more of an antimicrobial agent, a pigment, an anti-inflammatory agent, an anesthetic agent or a hemostatic agent.

The present disclosure also provides, in one embodiment, a method of preparing a film on a skin, comprising applying a suitable amount of a composition of any of the above embodiments on the skin and allowing the solvent to evaporate.

Further provided is a method of preparing an antimicrobial sealant on a skin, comprising applying a suitable amount of a composition of the present disclosure on the skin and allowing the solvent to evaporate.

Still provided, in one embodiment, is a method of preparing a body paint on a skin, comprising applying a suitable amount of a composition of the present disclosure on the skin and allowing the solvent to evaporate

DETAILED DESCRIPTION

As used herein, certain terms may have the following defined meanings. As used in the specification and claims, the singular form "a," "an" and "the" include singular and plural references unless the context clearly dictates otherwise. For example, the term "a film" includes a single film as well as a plurality of films, including mixtures thereof.

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this invention. Accordingly, it is intended that the methods and compositions can include additional steps and components (comprising) or alternatively including steps and compositions of no significance (consisting essentially of) or alternatively, intending only the stated method steps or compositions (consisting of).

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". The term "about" also includes the exact value "X" in addition to minor increments of "X" such as "X+0.1" or "X−0.1." It also is to be understood, although not always explicitly stated, that the reagents described herein are merely exemplary and that equivalents of such are known in the art.

It is to be understood that the terminology used herein is for the purpose of describing particular embodiments only and is not intended to limit the scope of the present specification. In this specification and in the claims that follow, reference will be made to a number of terms that shall be defined to have the following meanings:

"Aromatic" indicates that each of ring atoms is essentially in the same plane and has a p-orbital perpendicular to the ring plane, and in which (4n+2) π electrons, when n is 0 or a positive integer, are associated with the ring to comply with Huckel's rule. Aromatic ring systems may be depicted as a circle, which represents the (4n+2) π electrons, enclosed by an outer cyclic structure, such as, a hexagon or pentagon. For example, each of the rings in the compound of Formula 1 is aromatic.

"Alkyl" refers to monovalent saturated aliphatic hydrocarbyl groups having from 1 to 10 carbon atoms and, in some embodiments, from 1 to 6 carbon atoms. "$C_{x-y}$alkyl" refers to alkyl groups having from x to y carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

"Lower alkyl" refers to an alkyl with from 1 to 6 carbon atoms.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Lower alkoxy" refers to an alkoxy with from 1 to 6 carbon atoms.

"Amino" refers to the group —$NH_2$.

"Hydroxyamino" refers to the group —NHOH.

"Alkoxyamino" refers to the group —NHO-alkyl wherein alkyl is defined herein.

"Cyano" or "carbonitrile" refers to the group —CN.

"Epoxy" refers to a group containing an oxygen atom joined by single bonds to two adjacent carbon atoms, thus forming the three-membered epoxide ring.

"Anhydride" refers to a group having two acyl groups bound to the same oxygen atom. "Maliec anhydride" refers to the acid anhydride group of malice acid.

"Carboxyl", "carboxy" or "carboxylic acid" refers to —COOH or salts thereof.

The term "halogen" or "halo" refers to fluoro, bromo, chloro, and iodo.

"Hydroxy" or "hydroxyl" refers to the group —OH.

"Nitro" refers to the group —$NO_2$.

"Thiol" refers to the group —SH.

"Compound" and "compounds" as used herein refers to a compound encompassed by the generic formulae disclosed herein, any subgenus of those generic formulae, and any forms of the compounds within the generic and subgeneric formulae, including the racemates, stereoisomers, and tautomers of the compound or compounds.

"Stereoisomer" or "stereoisomers" refer to compounds that differ in the chirality of one or more stereocenters. Stereoisomers include enantiomers and diastereomers.

"Tautomer" refer to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

Unless indicated otherwise, the nomenclature of substituents that are not explicitly defined herein are arrived at by naming the terminal portion of the functionality followed by the adjacent functionality toward the point of attachment. For example, the substituent "arylalkyloxycabonyl" refers to the group (aryl)-(alkyl)-O—C(O)—.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group etc.) are not intended for inclusion herein. In such cases, the maximum number of such substitutions is three. For example, serial substitutions of substituted aryl groups with two other substituted aryl groups are limited to -substituted aryl-(substituted aryl)-substituted aryl.

Similarly, it is understood that the above definitions are not intended to include impermissible substitution patterns (e.g., methyl substituted with 5 fluoro groups). Such impermissible substitution patterns are well known to the skilled artisan.

A "hydrophilic group" refers to a group that is attracted to, and tends to be dissolved by water. A hydrophilic group has a tendency to interact with or be dissolved by water and other polar substances. In one aspect, a hydrophilic group is charge-polarized and capable of hydrogen bonding, enabling it to dissolve more readily in water than in oil or other hydrophobic solvents. Hydrophilic and hydrophobic molecules are also known as polar molecules and nonpolar molecules, respectively.

A "polar group" refers to a chemical group in which the distribution of electrons is uneven enabling it to take part in electrostatic interactions.

"Polymerization initiator" refers to an agent that promotes initiation of a polymerization reaction. A polymerization initiator, in one aspect, reacts with a monomer to form an intermediate compound capable of linking successively with a large number of other monomers into a polymeric compound. One type of initiators produce free radicals, such as peroxides and aliphatic azo compounds used to polymerize vinyl chloride, methyl methacrylate, and other monomers. In one aspect, a polymerization initiator is an anion. In another aspect, a polymerization initiator is a photoactive initiator, such as but not limited to alpha hydroxyketone, like Irgacure 184, Irgacure 2959 or DAROCUR®1173 from Ciba Specialty Chemicals Inc.

"Degree of polymerization" or "DP" refers to the number of monomeric units in a macromolecule or polymer or oligomer molecule. For a homopolymer, there is only one type of monomeric unit and the number-average degree of polymerization is given by total molecular weight divided by molecular weight of the monomer unit. For a copolymer, DP refers to the number of repeat units.

"Degree of hydrolysis" refers to the fraction of a compound, which has undergone hydrolysis at equilibrium. Hydrolysis is a chemical reaction of one compound with water, often resulting in the formation of one or more new compounds. For polyvinyl acetal, degree of hydrolysis is the percentage of dangling acetate on the polymer backbone, which has hydrolyzed to form dangling hydroxyl groups and free acetate.

"Degree of acetalization" refers to the molar percentage of hydroxyl group substitution via acetalization with aldehyde during the synthesis of polyvinyl acetal.

Unless otherwise defined, all technical and scientific terms used herein have the same meaning as commonly understood by one of ordinary skill in the art to which this disclosure belongs.

Film Forming Compositions

The present disclosure provides film forming compositions. The compositions can be non-toxic, coatable and sprayable. After application, the compositions can form flexible films quickly. The film can chemically react with skin, adhere to skin for prolonged time of period. Another advantage is that the composition can accommodate active ingredients, such as drugs, pigments, inorganic particles and antimicrobial agents for killing bacteria and viruses.

In one embodiment, the present disclosure provides, in one embodiment, a composition comprising, or alternatively consisting essentially of, or alternatively consisting of, polyvinyl acetal (PVA) and siloxane, wherein the siloxane comprises a hydrophilic group. Alternatively, the siloxane comprises a functional group or a polar group. In some aspects, the composition further comprises a solvent.

PVA demonstrates outstanding adhesion to many surfaces, is compatible with active ingredients, chemically and thermally stable and non-toxic. PVA can form flexible and water-repellent films. It is also noted that PVA has good solubility in alcohol and lower alkyl acetate.

PVA has long polymer chains, contributing to toughness combined with flexibility of the film. Along the long polymer chains, there are randomly distributed hydroxyl groups, acetate groups, and acetals, contributing to the outstanding binding efficiency and adhesion to a large number of surfaces because the hydroxyl groups, acetate groups and acetals interact with different groups on the surface for strong binding. The random distribution of the groups on the polymer chains minimizes the probability of crystallization, which in turn results in excellent optical clarity of the formed film. PVA films are characterized by high resistance to aliphatic hydrocarbons, mineral, animal and vegetable oils (with the exception of castor and blown oils).

Acetals offer stability against all types of nucleophiles and bases and most oxidants, so long as the conditions do not lead to hydrolysis of the acetal. Additionally, acetals withstand strong alkalis but are subject to some attack by strong acids. The stability of PVA film contributes to the compatibility with other active ingredients. For example, when ethanol is as the solvent, the film forms quickly in a matter of seconds via ethanol evaporation.

In the current technology, siloxane, as a plasticizer, is introduced to make the film flexible and to increase the gas permeability of the resultant film, making the film breathable. This feature will ultimately bring comfort to consumer.

One unexpected finding of the present disclosure is in view of the conventional wisdom that siloxane is inherently inert and shows poor adhesion to most surfaces. It is therefore widely perceived that siloxane does not serve as a good plasticizer for a film forming composition, which forms films that need to adhere to a surface. This is because the introduction of siloxane would undoubtedly result in weakened adhesion of the resultant film to the surface.

In the present technology, such negative effect of siloxane is eliminated by including one or more polar groups or alternatively hydrophilic groups into the siloxane. Such polar or hydrophilic groups help form either chemical bonds or strong electrostatic interactions with the surface such as skin. Chemical bonds are much stronger than physical interactions and thus can greatly enhance the adhesion. In this context, siloxane with polar or hydrophilic groups such as epoxy and maleic anhydride can be used as both a plasticizer and adhesion promoter.

It is further contemplated that, in one embodiment of the present disclosure, there is an absence of polymerization initiator in the film forming composition. Conventional film forming formulation of cyanoacrylate requires the presence of anions as initiators for starting the reaction in situ. In another aspect, a polymerization initiator is a chemical that generate free radicals, such as peroxides and aliphatic azo compounds. UV curing formulations usually need photoactive initiators to generate the first batch of free radicals under UV lights for subsequent polymerization. These UV initiators include alpha hydroxyketone, like Irgacure 184, Irgacure 2959 and DAROCUR®1173 from Ciba Specialty Chemicals Inc. In the present technology, no polymerization initiator is required for the formation of a flexible, breathable, durable and waterproof on skin. Associated with feature, another advantage of the present technology is apparent, that is, the absence of initiators and low molar mass olefinic monomers in the technology minimizes film toxicity due to residual initiator or monomers.

Mammalian skin is composed of three primary layers: a. the epidermis, which provides waterproofing and serves as a barrier to infection; b. the dermis, which serves as a location for the appendages of skin; c. the hypodermis (subcutaneous adipose layer). Epidermis is the outermost layer of the skin. It forms the waterproof, protective wrap over the body's surface and is made up of stratified squamous epithelium with an underlying basal lamina. The epidermis can be further subdivided into the following strata (beginning with the outermost layer): corneum, lucidum (only in palms of hands and bottoms of feet), granulosum, spinosum, basale. Cells are formed through mitosis at the basale layer. The daughter cells move up the strata changing shape and composition as they die due to isolation from their blood source. The cytoplasm is released and the protein keratin is inserted. They eventually reach the corneum and slough off. This process is called keratinization and takes place within about 27 days.

It is keratinization and the inert nature of keratin that make it difficult for film-forming compositions to adhere to the skin for a prolonged period of time. According to Wilkerson (Journal of Biological Chemistry, 107, 377, 1934), the stratum corneum has the following composition: cystine, 2.34%; tyrosine, 5.70%; histidine, 0.59%; lysine 3.08%; arginine, 10.01%. The primary amino group from lysine has great reactivity with epoxy and maleic anhydride under ambient conditions. Thus, lysine, for instance, from the skin, can be employed to react with siloxane having the corresponding reactive or functional group which is polar or hydrophilic, for greatly enhanced adhesion.

Polyvinyl Acetals (PVA)

Methods of preparing polyvinyl acetals (PVA) are well known in the art. For instance, PVA can be prepared from aldehydes and polyvinyl alcohols. Acetals are formed by the well-known reaction between aldehydes and alcohols. The addition of one molecule of an alcohol to one molecule of an aldehyde produces a hemiacetal. Hemiacetals are rarely isolated because of their inherent instability, but, rather, are further reacted with another molecule of alcohol to form a stable acetal.

Polyvinyl alcohols are high molecular weight resins containing various percentages of hydroxyl and acetate groups produced by hydrolysis of polyvinyl acetate. The conditions of the acetal reaction and the concentration of the particular aldehyde and polyvinyl alcohol used are closely controlled to form polymers containing predetermined proportions of hydroxyl groups, acetate groups and acetal groups. The final product may be represented by the following stylized structure. The proportions of A, B and C are controlled, and they are randomly distributed along the molecule.

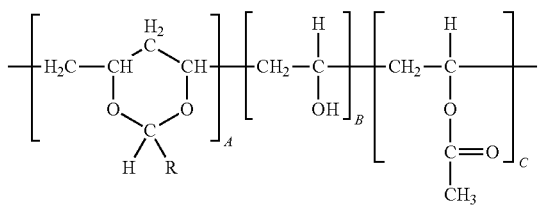

Here R can be methyl, ethyl, propyl, butyl, hexyl, benzyl group and combinations thereof. A can be an integer in the range of from about 50 to about 1800, or from 100 to about 1000; B can be an integer in the range of from about 10 to about 800, or from about 100 to about 500; and C can be an integer from the range of 0 to about 1000, or from about 100 to about 500.

In one aspect, the polyvinyl alcohol has a molecular weight from about 25,000 to about 250,000, or alternatively from about 50,000 to about 200,000, or alternatively from about 75,000 to about 175000, or alternatively from about 100,000 to about 150,000.

In another aspect, the polyvinyl alcohol has a degree of polymerization of from about 200 to about 2,000, or alternatively from about 300 to about 1500, or alternatively from about 400 to about 1200, or alternatively from about 400 to about 800.

In some aspects, the polyvinyl alcohol has a degree of hydrolysis greater than about 70 mol %, or alternatively about 80 mol %, or about 85 mol %, or about 90 mol %, or about 95 mol %, or about 98 mol %, or about 99 mol %. In some aspects, the polyvinyl alcohol has a degree of hydrolysis that is lower than about 99.99 mol %, or alternatively lower than about 99.9 mol %, or alternatively lower than about 99 mol %, or alternatively lower than about 98 or 95 mol %. It is noted that when the degree of hydrolysis is too low, the solubility in water is low and polyvinyl alcohol is difficult to produce from it. On the other hand, polyvinyl alcohol having a too high degree of hydrolysis is difficult to produce.

Polyvinyl alcohol can be acetalized into polyvinyl acetal under an acidic condition in an aqueous solvent according to a known method. The polyvinyl acetal thus obtained herein, in one aspect, has a degree of acetalization of from about 45 to about 90 mol %. Alternatively, the degree of acetalization is from about 50 to about 85 mol %, or from about 55 to about 80 mol %, or from about 60 to about 75 mol %. Polyvinyl alcohol with too low a degree of acetalization is unfavorable since the powdery reaction product obtained through acetalization can be difficult to recover and since the waterproofness of the polyvinyl acetal obtained can be low or the compatibility of polyvinyl acetal with plasticizer can be low. When the degree of acetalization of polyvinyl acetal is too high, the polyvinyl acetal of the type can be difficult to produce, and its compatibility with plasticizer may be lowered.

The aldehyde compound to be used for the acetalization includes, for example, formaldehyde, acetaldehyde, propionaldehyde, butylaldehyde, hexylaldehyde and benzaldehyde. These may be used singly or as a mixture of two or more of them. In some aspects, the aldehyde compounds are alkyaldehyde having at most four carbon atoms and benzaldehyde and butylaldehyde are preferred.

There are commercially available polyvinyl acetal resins, like polyvinyl formal acetal and polyvinyl butyral. For example, polyvinyl butyral resins are sold by Solutia under the name of Butvar®, and by Kuraray under the name of Mowital®. Butvar® B-72, B-74, B-76, B-79, B-90, and B-98 are polyvinyl butyrals with molecular weights between 40 and 250 kg/mol, butyral content expressed as % polyvinyl butyral between 80 and 88%; acetate content expressed as % polyvinyl acetate between 0.0 and 2.5%; hydroxyl content expressed as % polyvinyl alcohol between 11.5 and 20%. Mowital® B20H, B30T, B30H, B30HH, B45H, B60T, B60H, B60HH, and B75H have molecular weights from 20 to 100 kg/mol.

A particular example of PVA is polyvinyl butyral (PVB). In one aspect, a polyvinyl butyral content of between about 70 and about 90% weight of the total polymer is used. Alternatively, the content is from about 72 to about 85%, or from about 73 to about 80%, or about 75%.

Examples of polyvinyl butyrals resins and properties of such resins are disclosed in the brochures provided by Solutia Inc. and Kuraray America Inc. These PVB polymers can be used singly or mixed with one or more other grades. Exemplary polyvinyl butyrals are Butvar® B-72, Butvar® B-74, Butvar® B-76, Butvar® B-79 and Butvar® B-98. The content of PVB is preferably within a range of 0.1 wt/vol % to 60 wt/vol % based on the solvent, and more preferably within a range of 1-30 wt/vol % in view of the resultant film flexibility and adhesion to skin.

Siloxane

A siloxane is any chemical compound composed of units of the form $R_2SiO$, where R is a hydrogen atom or a hydrocarbon group, as well as their derivatives. Siloxanes can have branched or unbranched backbones consisting of alternating silicon and oxygen atoms —Si—O—Si—O—, with side chains R attached to the silicon atoms.

In some aspects, the siloxane has a structure of:

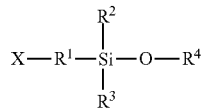

wherein:

X is selected from the group consisting of an amino group, an epoxy group, a hydroxyl group, a carboxylic acid group, and a maleic anhydride group;

$R^1$ is a divalent organic group optionally substituted with an oxygen, nitrogen, or sulfur atom, or is selected from the group consisting of a substituted or non-substituted $C_2$-$C_{20}$-aliphatic group, a substituted or non-substituted aromatic group, and a substituted or non-substituted aliphatic aromatic group;

$R^2$ and $R^3$ are independently selected from the group consisting of a lower alkyl group, a lower alkoxy group, and a polymeric siloxane group;

$R^4$ is selected from the group consisting of a lower alkyl group, an oligomeric or a polymeric siloxane group and

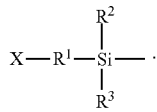

In one aspect, X is selected from the group consisting of an amino group, an epoxy group, a hydroxyl group, a carboxylic acid group, and a maleic anhydride group. In another aspect, $R^1$ is a divalent organic group optionally substituted with an oxygen, nitrogen, or sulfur atom, or is selected from the group consisting of a substituted or non-substituted $C_2$-$C_{20}$-aliphatic group, a substituted or non-substituted aromatic group, and a substituted or non-substituted aliphatic aromatic group. In yet another aspect, $R^2$ is selected from the group consisting of a lower alkyl group, a lower alkoxy group, and a polymeric siloxane group. In still another aspect, $R^3$ is selected from the group consisting of a lower alkyl group, a lower alkoxy group, and a polymeric siloxane group. In another aspect, $R^4$ is selected from the group consisting of a lower alkyl group, an oligomeric or a polymeric siloxane group and

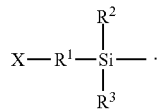

In one aspect, the hydrophilic group comprises one or more of the group of halogen, oxygen, nitrogen, sulfur or phosphorus. In another aspect, the hydrophilic group is one or more of the group of a carboxylic acid, an amino group, a hydroxyl group, an epoxy group or an anhydride group.

Examples of the hydrophilic group include, without limitation,
(3-glycidoxypropyl)dimethylethoxysilane,
(3-glycidoxypropyl)pentamethyldisiloxane,
(3-glycidoxypropyl)methyldiethoxysilane,
(3-glycidoxypropyl)triethoxysilane,
5,6-epoxyhexyltriethoxysilane,
(3-glycidoxypropyl)bis(trimethylsiloxy)methylsilane,
1,3-bis(glycidoxypropyl)tetramethyldisiloxane,
1,5-bis(glycidoxypropyl)-3-phenyl-1,1,3,5,5-pentamethyl-trisiloxane,
bis[2-(3,4-epoxycyclohexyl)ethyl]tetramethyldisiloxane,
mono-(2,3-epoxy)propylether terminated polydimethylsiloxane,
epoxypropoxypropyl terminated polydimethylsiloxane,
epoxycyclohexylethyl terminated polydimethylsiloxane,
epoxypropylheptaisobutyl-T8-silsesquioxane,
succinic anhydride terminated polydimethylsiloxane,
bis(2-hydroxyethyl)-3-aminopropyltriethoxysilane,
1,3-bis(hydroxypropyl)tetramethyldisiloxane,
1,3-bis(hydroxybutyl)tetramethyldisiloxane,
monocarbinol terminated polydimethylsiloxane,
3-[hydroxy(polyethyleneoxy)propyl]heptamethyltrisiloxane,
trimethylsilylpropionic acid,
1,3-bis(3-carboxypropyl)tetramethyldisiloxane, or
3-(triethoxysilyl)propylsuccinic anhydride.

Siloxanes are commercially available from various vendors.

The content of silanol groups in the siloxane after modification is preferably within a range of from 0.1 wt. % to 60 wt. % based on the resin so modified, and more preferably within a range of 3-40 wt. % in view of the processability and adhesion.

Solvents

The solvent in the disclosed compositions can be inorganic or organic. Examples of the organic solvent include, without limitation, alcohols such as methanol, ethanol, isopropanol, n-propanol, butanol; cellosolves such as methyl cellosolve, butyl cellosolve; ketones such as acetone, methyl ethyl ketone; aromatic hydrocarbons such as toluene, xylene; and halohydrocarbons such as dichloromethane, chloroform; alkyl acetate, such as methyl acetate, ethyl acetate, propyl acetate, isopropyl acetate, butyl acetate, isobutyl acetate, amyl acetate, isoamyl acetate, heptyl acetate, octyl acetate, nonanyl acetate, decyl acetate; aromatic acetate, such as benzyl acetate. One or more of these may be used herein either singly or as combined. Among these solvents, ethanol is more preferred. Other examples include methanol, ethanol, isopropanol, n-propanol, butanol, methyl cellosolve, butyl cellosolve, alkyl acetate, acetone, methyl ethyl ketone, toluene, xylene, dichloromethane or chloroform.

Non-limiting examples of inorganic solvent include water, saline or combinations thereof.

Additives

In some embodiments, the composition can contain any known ordinary additives such as UV absorbent, light stabilizer, antioxidant, surfactant, or colorant.

Traditional plasticizers for polyvinyl acetals are tri or tetraethylene glycol dicarboxylates such as triethylene glycol di-2-ethylhexanoate, tetraethylene glycol di-2-ethylhexanoate, triethylene glycol di-n-heptanoate, tetraethylene glycol di-n-deptanoate; and dicarboxylates such as dioctyl adipate, dibutyl adipate, dioctyl phthalate and dibutyl phthalate. One or more of these may be used herein either singly or as combined.

Antimicrobial Agents

Antimicrobial agents are chemical compounds that destroy microbes, prevent their pathogenic action, or prevent their growth. Antimicrobial agents, often referred to as anti-infective agents, are frequently applied topically to the skin and mucous membranes in the form of a solution, cream, or ointment; appropriate formulations may be applied to wound and body cavities, and to the eyes, nose and mouth.

Examples of antimicrobial agents include, without limitation, silver particles, silver compounds like silver chloride, silver acetate, silver oxide, silver sulfate, silver nitrate, silver thiosulfate and combinations thereof. The antimicrobial activity of inorganic substances is generally related to the ions into which they dissociate. The antimicrobial activity of various metal ions, for example, is often attributed to their affinity for protein material and the insolubility of the metal proteinate formed.

Quaternary ammonium cations, also known as quats, another type of antimicrobial agent, are positively charged polyatomic ions of the structure $NR_4^+$, R being an alkyl group. Unlike the ammonium ion ($NH_4^+$) and the primary, secondary, or tertiary ammonium cations, the quaternary ammonium cations are permanently charged, independent of the PH of their solution. Quaternary salts are another type of antimicrobial agents, with a general structure shown below:

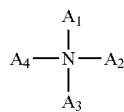

where $A_1$, $A_2$, $A_3$ and $A_4$ can each be, independent of one another, hydrogen, an alkyl, halogenated alkyl, alkenyl, alkynyl, aryl, heteroaryl, cycloalkyl, cycloalkenyl, heterocycloalkyl, or heterocycloalkenyl group described above. Also, any of the $A_1$, $A_2$, $A_3$ and $A_4$ substituents can be absent and any of the remaining substituents can be a multivalent group. Certain quaternary ammonium compounds, especially those containing long alkyl chains, are used as antimicrobials and disinfectants. Examples are benzalkonium chloride, benzethonium chloride, methylbenzethonium chloride, cetalkonium chloride, cetylpyridinium chloride, cetrimonium, cetrimide, dofanium chloride, tetraethylammonium bromide, didecyldimethylammonium chloride and domiphen bromide. Also good against fungi, amoeba, and enveloped viruses, quats act by disrupting the cell membrane. Quaternary ammonium compounds are lethal to a wide variety of organisms except endospores, *Mycobacterium tuberculosis*, non-enveloped viruses, and *Pseudomonas* spp.

The use of acid-anionic surfactants as antibacterial agents is also known. Suitable surfactants may include sodium lauryl sulfate, linear alkylbenzene sulfonates, alcohol sulfates, alkyl sulfates, alkyl sulfonates, sodium alkyl methyltaurines, alpha-olefin sulfonates, alcohol ethoxylates, nonylphenyl ethoxylates, alkylpolyglucosides, fatty alcohols, fatty acids and fatty acid salts, lignosulfonates and lignin derivatives, hydroxypoly(oxyethylene) derivatives, fatty alkanolamides, fatty amine oxides, sodium dioctylsulfosuccinate, dodecylbenzene sulfonic acid and salts thereof, the sodium salt of sulfonated oleic acid, sodium dodecylbenzene sulfonate, lauramine oxide, dodecyldiphenyloxide-disulfonic acid and salts thereof.

Further examples of surfactants include alkyl(C8-C24) benzenesulfonic acid and its ammonium, calcium, magnesium, potassium, sodium, and zinc salts; alkyl(C8-C18) sulfate and its ammonium, calcium, isopropylamine, magnesium, potassium, sodium, and zinc salts; diethylene glycol abietate, lauryl alcohol, lignosulfonate and its ammonium, calcium, magnesium, potassium, sodium, and zinc salts; nonyl, decyl, and undecyl glycoside mixture with a mixture of nonyl, decyl, and undecyl oligosaccharides and related reaction products (primarily decanol and undecanol) produced as an aqueous based liquid (50 to 65% solids) from the reaction of primary alcohols (containing 15 to 20% secondary alcohol isomers) in a ratio of 20% C9, 40% C10, and 40% C11 with carbohydrates (average glucose to alkyl chain ratio 1.3 to 1.8); alpha-(o,p-dinonylphenyl)-omega-hydroxypoly(oxyethylene) mixture of dihydrogen phosphate and monohydrogen phosphate esters and the corresponding ammonium, calcium, magnesium, monethanolamine, potassium, sodium, and zinc salts of the phosphate esters; the poly(oxyethylene) content averages 4-14 moles; alpha-(p-nonylphenyl)-.omega.-hydroxypoly(oxyethylene) mixture of dihydrogen phosphate and monohydrogen phosphate esters and the corresponding ammonium, calcium, magnesium, monethanolamine, potassium, sodium, and zinc salts of the phosphate esters, the poly(oxyethylene) content averages 4-14 moles or 30 moles; .alpha.-(p-nonylphenyl)-.omega.-hydroxypoly(oxyethylene) produced by the condensation of 1 mole nonylphenol with an average of 4-14 moles or 30-90 moles ethylene oxide; .alpha.-(p-nonylphenyl)-.omega.-hydroxypoly(oxyethylene)sulfate, ammonium, calcium, magnesium, potassium, sodium, and zinc salts; octyl and decyl glucosides mixture with a mixture of octyl and decyloligosaccharides and related reaction products (primarily n-decanol) produced as an aqueous based liquid (68-72% solids) from the reactions of straight chain alcohols (C8 (45%), C10 (55%)) with anhydrous glucose; oxidized pine lignin and its salts thereof; beta-pinene polymers; polyethylene glycol .alpha.-hydro-.omega.-hydroxypoly(oxyethylene)); mean molecular weight of 194 to 9500 amu; .alpha.-(p-tert-Butylphenyl)-. omega.-hydroxypoly(oxyethylene) mixture of dihydrogen phosphate and monohydrogen phosphate esters and the corresponding ammonium, calcium, magnesium, monethanolamine, potassium, sodium, and zinc salts of the phosphate esters; the poly(oxyethylene) content averages 4-12 moles; .alpha.-(o,p-dinonylphenyl)-omega-hydroxypoly(oxyethylene) produced by the condensation of 1 mole of dinonylphenol with an average of 4-14 or 140-160 moles of ethylene oxide; sodium or potassium salts of fatty acids; sodium .alpha.-olefinsulfonate (sodium C14-C16) (Olefin sulfonate); sodium diisobutylnaphthalene sulfonate and/or sodium isopropylisohexylnaphthalene sulfonate; sodium dodecylphenoxybenzenedisulfonate; sodium lauryl glyceryl ether sulfonate; sodium oleyl sulfate; sodium N-lauroyl-N-methyltaurine, sodium N-palmitoyl-N-methyltaurine and/or sodium N-oleoyl-N-methyltaurine; sodium monoalkyl and dialkyl (C8-C16) phenoxybenzenedisulfonate mixtures containing not less than 70% of the monoalkylated products; 2,4,7,9-tetramethyl-5-decyn-4,7-diol; and/or nonylphenol ethoxylates with average moles of ethoxylation between 4 and 30.

Further, in other embodiments the surfactant may be one or more of the following alcohol ethoxylates: alpha-Alkyl(C9-C18-omega-hydroxypoly(oxyethylene) with polyoxyethylene content of 2-30 moles; .alpha.-(p-alkylphenyl)-omega.-hydroxypoly(oxyethylene) produced by the condensation of 1 mole of alkylphenol (alkyl is a mixture of propylene tetramer and pentamer isomers and averages C13) with 6 moles ethylene oxide; .alpha.-Alkyl(C6-C14-.omega.-hydroxypoly(oxypropylene) block copolymer with polyoxyethylene; polyoxypropylene content is 1-3 moles; polyoxyethylene content is 4-12 moles; average molecular weight is approximately 635 amu; .alpha.-Alkyl (C12-C15-.omega.-hydroxypoly(oxypropyylene)poly(oxyethylene) copolymers (where the poly(oxypropylene) content is 3-60 moles and the poly(oxyethylene) content is 5-80 moles; alpha-(p-Dodecylphenyl)-.omega.-hydroxypoly(oxyethylene) produced by the condensation of 1 mole of dodecylphenol with an average of 4-14 or 30-70 moles ethylene oxide; ethylene oxide adducts of 2,4,7,9-tetramethyl-5-decynediol, the ethyelene oxide content averages 3.5, 10, or 30 moles; alpha-Lauryl.omega.-hydroxypoly(oxyethylene), sodium salt; the poly(oxyethylene) content is 3-4 moles; secondary alkyl (C11-C15) poly(oxyethylene) acetate salts; ethylene oxide content averages 5 moles; alpha.-[p-1,1,3,3-tetramethylbutyl)phenyl-]-.omega.-hydroxypoly(oxyethylene) produced by the condensation of 1 mole of p-1,1,3,3-tetramethylbutylphenol with a range of 1-14 or 30-70 moles ethylene oxide; tridecylpoly(oxyethylene) acetate salts where the ethylene oxide content averages 6-7 moles; poly(oxy-1,2-ethanediyl), .alpha.-(carboxymethyl)-.omega.-(nonylphenoxy) produced by the condensation o 1 mole nonylphenol with an average of 4-14 or 30-90 moles ethylene oxide with a molecular weight in the ranges 454-894 and 1598-4238; and/or .alpha.-Stearoyl-.omega.-hydroxy(polyoxyethylene), polyoxyethylene content averages either 8, 9, or 40 moles.

Colorant or Pigments

A pigment is a colored, black, white, or fluorescent particulate organic or inorganic solid. These solids are usually insoluble in, and essentially physically and chemically unaffected by, the vehicle or substrate into which it is incorporated. FDA-approved pigments includes iron oxides, titanium dioxide, extender pigments ultramarine pigments, manganese violet, mixed metal oxide pigments, fluorescent pigments, carbon black, magnetite, lodestone, magnetic iron oxide. Ultramarine pigments are insoluble inorganic compounds that are available in a wide range of blue shades, green shades, violets, and pink. Manganese violet is FDA approved for cosmetic applications. It has excellent lightfastness (8) and bleed resistance (5).

Zinc oxide is recognized as a mild antimicrobial, wound healing and sunscreen agent. It primarily absorbs UVA light rather than scattering or reflecting, non-irritating, non-comedogenic, and micronized by forming many small micro particles for cosmetic use. Titanium dioxide is derived from Titanium, a highly reflective white chalky mineral, non-irritating, non-comedogenic, micronized by forming many small micro particles for cosmetic use, listed in the FDA monograph as one of the top and most effective active ingredients for sun protection. Titanium dioxide is the most important white pigment currently produced commercially. The pigment is used in a wide range of applications including inks, textiles, paper, paints, food, and pharmaceuticals. Pure titanium dioxide ($TiO_2$) is stable, nonvolatile, and largely insoluble. Regular titanium dioxide is highly stable under most conditions. However, it has some photocatalytic activity (i.e. promotes reactions between other chemicals), especially in direct sunlight. Titanium dioxide nanoparticles appear to have much greater photocatalytic activity than regular titanium dioxide powder and might trigger formation of harmful free radicals when exposed to sunlight. Most manufacturers of titanium dioxide nanoparticles coat them to reduce or eliminate such effects.

Titanium dioxide is a physical sunscreen protecting against UVB and short UVA (a.k.a. UNA-1) light. It has a long history of seemingly safe use and is not irritating. Its disadvantages include unsightly whitish tint and insufficient protection against long UVA (a.k.a. UVA-2). It may also help generate harmful free radicals via photocatalytic mechanism when exposed to sunlight. These effects may not have significant impact in topical use but the issue needs to be researched. Nanoparticle forms of titanium dioxide are less unsightly but their potential risks are unclear and may be greater than those associated with regular forms. More research is clearly needed. To increase protection and extend its range, titanium dioxide is usually combined with chemical UVB and UVA blockers and/or zinc oxide.

The main complaint about titanium dioxide-based sunscreens is that they leave unsightly white residue. In fact, titanium dioxide creates stronger whitish tint than zinc oxide at comparable concentrations. This problem has been partly addressed by the advent of titanium dioxide nanoparticles as a sunscreen agent. Titanium dioxide nonoparticles have different optical properties and tend to produce much less whitish tint than regular powdered titanium dioxide. Yet, early research indicates that titanium dioxide nanoparticles retain the capacity to protect from UVB and short UVA (UVA-2) light. However, the safety of titanium dioxide nanoparticles remains a controversial subject. When exposed to sunlight (and possibly even other light), titanium dioxide nanoparticles may promote generation of free radicals and increase the risk of mutations—more so that regular titanium dioxide. Furthermore, in one UCLA study, titanium dioxide nanoparticles administered orally to mice in water were shown to cause genetic damage, such as mutations and DNA breaks. However, this effect may not be relevant to topical use as long as titanium dioxide nanoparticles do not penetrate stratum corneum (the outer skin layer consisting mostly of dead cells). Furthermore, manufacturers typically cover titanium dioxide nanoparticles with special coating, which increases the stability and reduces photoreactivity of the particles. Finally, there is a question whether titanium dioxide nanoparticles, could penetrate the skin, reach systemic circulation and accumulate in body organs. At present, there is no clear evidence that they do, but this is a valid concern that needs to be researched. Until then, it may be prudent to avoid the products with titanium dioxide nanoparticles (regular titanium dioxide should be ok).

Titanium dioxide is in many ways similar to zinc dioxide as a sun blocking agent. However, zinc oxide has advantages of having broader range, anti-irritant properties and less opacity at comparable concentrations. In commercial sunscreens, titanium dioxide is usually combines with chemical UVB blockers. Sometimes it is also combined with other physical (zinc oxide) and/or chemical UVA blockers.

Anti-Inflammatory/Anesthetic Agents

Inflammation is the body's response to irritation or injury, and is characterized by redness, warmth, swelling, and pain. Anti-inflammatory refers to the property of a substance or treatment that reduces inflammation. Non-steroidal anti-inflammatory drugs (NSAIDs), alleviate pain by counteracting the cyclooxygenase (COX) enzyme. On its own COX enzyme synthesizes prostaglandins, creating inflammation. In whole the NSAIDs prevent the prostaglandins from ever being synthesized, reducing or eliminating the pain. Some common examples of NSAIDs are: aspirin, ibuprofen, and naproxen. NSAIDs are used to treat a variety of conditions that cause inflammation. NSAIDs are also used to treat pain from injury or other causes of long-term pain. NSAID can reduce inflammation and relieve pain, and these drugs include ibuprofen, naproxen sodium, aspirin, ketoprofen, procaine, cocaine, lidocaine, prilocaine, bupivacaine, levobupivacaine, ropivacaine, and dibucaine.

Local anesthetics are agents that prevent transmission of nerve impulses without causing unconsciousness. They act by binding to fast sodium channels from within (in an open state). Local anesthetics can be either ester or amide based. Ester local anesthetics (e.g., procaine, amethocaine, cocaine) are generally unstable in solution and fast-acting, and allergic reactions are common. Amide local anesthetics (e.g., lidocaine, prilocaine, bupivicaine, levobupivacaine, ropivacaine, mepivacaine and dibucaine) are generally heat-stable, with a long shelf life (around 2 years). They have a slower onset and longer half-life than ester anaesthetics, and are usually racemic mixtures, with the exception of levobupivacaine (which is S(–)-bupivacaine) and ropivacaine (S(–)-ropivacaine). These agents are generally used within regional and epidural or spinal techniques, due to their longer duration of action, which provides adequate analgesia for surgery, labor, and symptomatic relief.

Hemostatic Agents

Antihemorrhagic agents used in medicine have various mechanisms of action. Systemic drugs work by inhibiting fibrinolysis or promoting coagulation. Locally-acting hemostatic agents work by causing vasoconstriction or promoting platelet aggregation. There are several widely used hemostatic materials, including oxidized regenerated cellulose, gelatin, fibrin, thrombin, alginate, zeolite, collagen and chitosan. For example, microfibrillar collagen hemostat (MCH) is a topical agent composed of resorbable microfibrillar collagen. It attracts platelets and allows for the formation of a blood clot when it comes into contact with blood. Unlike the hemostatic clamp, no mechanical action is involved. The surgeon presses the MCH against a bleeding site, and the collagen attracts and helps with the clotting process to eventually stop bleeding. The practical application for MCH is different from that of the hemostatic clamp. It is not possible, for example, to stop a severed artery from gushing blood by using a patch of MCH and wait for the clotting process. The blood vessel must be mechanically clamped and repaired.

Methods and Kits

The composition of any of the above embodiment can be provided in a gel, solid, or liquid form, or can be prepared in a form that is pharmaceutically acceptable.

In one embodiment, the present disclosure provides a composition prepared by admixing PVA and siloxane in a solvent, wherein the siloxane comprises a hydrophilic group. Examples of PVA, siloxane, solvent and hydrophilic group are provided above and generally in the disclosure.

Also provided, in one embodiment, is a film that is obtained by reducing the content of the solvent in a composition of any of the above embodiments, or a film that is obtainable by reducing the content of the solvent in a composition of any of the above embodiments. In one aspect, the solvent is reduced by evaporation.

Kits are also provided, comprising, in two or more separate compartments, polyvinyl acetal (PVA), siloxane and a solvent. In some aspects, the kit further comprises one or more of an antimicrobial agent, a pigment, an anti-inflammatory agent, an anesthetic agent or a hemostatic agent.

The present disclosure also provides, in one embodiment, a method of preparing a film on a skin, comprising applying a suitable amount of a composition of any of the above embodiments on the skin and allowing the solvent to evaporate.

Further provided is a method of preparing an antimicrobial sealant on a skin, comprising applying a suitable amount of a composition of the present disclosure on the skin and allowing the solvent to evaporate.

Still provided, in one embodiment, is a method of preparing a body paint on a skin, comprising applying a suitable amount of a composition of the present disclosure on the skin and allowing the solvent to evaporate.

Compositions, Methods and Kits without the Solvent

It is also contemplated that any of above compositions or kits can be provided without the corresponding solvent. For the kits, the solvent can be provided in a separate compartment or package. In one aspect, the compositions or kits contain all the recited ingredients without a solvent. Before using the compositions or kits, the user can simply add a suitable amount of solvent to the composition or kit. Accordingly, relevant instructions can be provided, along with the compositions or kits.

In another aspect, the solvent can be removed, or partially removed, from any of the compositions or kits, for the purpose of, e.g., storage or transportation. Removal of the solvent can be done with methods readily available in the art, as illustrated in Example 7, without allowing the composition to form a film during the process. For instance, freeze-drying (also known as lyophilisation, lyophilization or cryodesiccation) is a dehydration process typically used to preserve a perishable material or make the material more convenient for transport. Freeze-drying works by freezing the material and then reducing the surrounding pressure and adding enough heat to allow the frozen water in the material to sublime directly from the solid phase to the gas phase. The original compositions can be regenerated by adding proper amount of solvent to these solid, semi-solid, or gel-like, components following the same procedures described in the invention. This regeneration of composition will not adversely affect the performance.

Likewise, methods of preparing and using the compositions or kits, without the solvent, are also provided.

EXAMPLES

The present invention is further defined by reference to the following examples. It will be apparent to those skilled in the art that many modifications, both to threads and methods, may be practiced without departing from the scope of the current invention.

Example 1

Antimicrobial Sealant

This example provides a antimicrobial sealant that can be useful, for example, for minimizing surgical site infections.

According to the CDC, each year in the US almost 500,000 surgical site infections (SSIs) occur, making them the second most-common healthcare-associated infection. In clean surgeries, direct inoculation of the patient's own skin flora is the primary source of incisional contamination. Because the skin cannot be completely sterilized and rebound growth of bacteria deep in the skin occurs during surgery. There are two ways to minimize SSI, maintaining a normal body temperature and using microbial sealants.

In this example, 1.0 g of PVB (90000~120000 g/mol, Butvar® B 76 from Solutia, Inc.) was transferred to a flask (250 ml) filled with 200 proof ethanol (100 ml). The mixture was stirred for 5 hours to dissolve all PVB particles. Then 30 mg of (3-glycidoxypropyl)pentamethyldisiloxane was added to the solution above and the mixture was further stirred for 30 min.

Using a brush, fingertip, or swab, a few droplets of the composition can be spread on a surface area of 4 inch$^2$. Upon contact with the prepped skin, the film-forming composition above quickly forms a thin, flexible film which bonds to the skin surface, including skin contours, hair follicles and sweat glands. This breathable film immobilizes bacteria which survive the conventional surgical skin preparation and rebound during surgery, preventing migration or transference into the incision.

This film has a unique mechanism of action which reduces skin Row contamination by physically immobilizing microorganisms—not by antimicrobial activity. Using the film-forming composition as microbial sealant does not contribute to antimicrobial resistance, therefore.

Example 1A

Antimicrobial Sealant

In this example, 1.0 g of PVB (90000~120000 g/mol, Butvar® B 76 from Solutia, Inc.) was transferred to a flask (250 ml) filled with methyl acetate (100 ml). The mixture was stirred for 5 hrs to dissolve all PVB particles. Then 30 mg of (3-glycidoxypropyl)pentamethyldisiloxane was added to the solution above and the mixture was further stirred for 30 min.

Example 1B

Antimicrobial Sealant

In this example, 1.0 g of PVB (50000~80000 g/mol, Butvar® B 79 from Solutia, Inc.) was transferred to a flask (250 ml) filled with ethyl acetate (100 ml). The mixture was stirred for 5 hrs to dissolve all PVB particles. Then 30 mg of 1,3-bis (glycidoxypropyl)tetramethyldisiloxane, was added to the solution above and the mixture was further stirred for 30 min.

Example 1D

Antimicrobial Sealant

In this example, 1.0 g of PVB (50000~80000 g/mol, Butvar® B 79 from Solutia, Inc.) was transferred to a flask (250 ml) filled with isopropyl acetate (100 ml). The mixture was stirred for 5 hrs to dissolve all PVB particles. Then 30 mg of epoxypropoxypropyl terminated polydimethylsiloxane was added to the solution above and the mixture was further stirred for 30 min.

Example 1E

Antimicrobial Sealant

In this example, 1.0 g of PVB (50000~80000 g/mol, Butvar® B 79 from Solutia, Inc.) was transferred to a flask (250 ml) filled with butyl acetate (100 ml). The mixture was stirred for 5 hrs to dissolve all PVB particles. Then 30 mg of 1,3-bis (hydroxybutyl)tetramethyldisiloxane was added to the solution above and the mixture was further stirred for 30 min.

Example 2

Liquid Bandage

Liquid bandage is a typical film forming composition, which is a topical skin treatment for minor cuts and sores that is sold by several companies. The products are mixtures of chemicals which create a polymeric layer which binds to the skin. This protects the wound by keeping dirt and germs out, and keeping moisture in. Compared to traditional bandages, liquid bandages are waterproof and germ-proof and can speed and enhance healing, and stay on for days. Liquid bandages can also be applied to some hard-to-reach areas, like the space between fingers.

In this example, 30 g of PVB (50000~80000 g/mol, Butvar® B-79 from Solutia, Inc.) was transferred to a flask (250 ml) filled with 200 proof ethanol (100 ml). The mixture was stirred for 5 hrs to dissolve all PVB particles. Then 12 g of 3-(triethoxysilyl)propylsuccinic anhydride was added to the solution above and the mixture was further stirred for 30 min.

Then either or both of the following ingredients were added: enzethonium chloride (0.2%) and lidocaine HCl (2.5%), to the mixture. Thus, a liquid bandage with antiseptic and anesthetic effect was formulated.

Example 3

Body Paints/Scar Camouflage

In this example, 30 g of PVB (40000~70000 g/mol, Butvar® B-98 from Solutia, Inc.) was transferred to a flask (250 ml) filled with 200 proof ethanol (100 ml). The mixture was stirred for 5 hrs to dissolve all PVB particles. Then 12 g of mono-(2,3-epoxy)propylether terminated polydimethylsiloxane (Mw~1000 g/mol), was added to the solution above and the mixture was further stirred for 30 min.

To the composition above 2.0 wt % red pigment (Derma #17AA) was added. The formulation was then shaken well to form a stable dispersion. A water-repellent, breathable, non-tacky body paint was then fabricated with long-lasting time on skin.

Example 4

Water-Proof Sun Block

In this example, 10 g of PVB (120000~150000 g/mol, Butvar® B-74 from Solutia, Inc.) was transferred to a flask (250 ml) filled with 200 proof ethanol (100 ml). The mixture was stirred for 5 hrs to dissolve all PVB particles. Then 2 g of 1,3-bis(hydroxypropyl)tetramethyldisiloxane was added to the solution above and the mixture was further stirred for 30 min.

When zinc oxide (10 wt %) and titanium oxide (10 wt %) particles were added to the formulation, a sun block with broad spectrum of blockade was made. The sun block stayed on skin for extended period and was not abraded off easily.

Example 5

Makeup Sealer

A makeup sealer is a water-resistant, anti-perspiring coating on a completed makeup. When a perfume (Calone or methylbenzodioxepinone, trade-named Calone 1951 from Pfizer Inc.) (0.05%) is added to the composition, a makeup sealer is created and can be sprayed to the final makeup to form a flexible, water-repellent film to bind the makeup onto skin even in a hot summer day or on heavily perspiring skins.

In this example, 2 g of PVB (170000~250000 g/mol, Butvar® B-72 from Solutia, Inc.) was transferred to a flask (250 ml) filled with 200 proof ethanol (100 ml). The mixture was stirred for 5 hrs to dissolve all PVB particles. Then 0.6 g of 3-[hydroxy(polyethyleneoxy)propyl]heptamethyltrisiloxane was added to the solution above and the mixture was further stirred for 30 min.

Example 6

Antimicrobial Wipe/Spray

In this example, 2 g of PVB (170000~250000 g/mol, Butvar® B-72 from Solutia, Inc.) was transferred to a flask (250 ml) filled with 200 proof ethanol (100 ml). The mixture was stirred for 5 hrs to dissolve all PVB particles. Then 0.4 g of 1,3-bis(3-carboxypropyl)tetramethyldisiloxane was added to the solution above and the mixture was further stirred for 30 min.

When a biocide (benzethonium chloride, 0.85 wt %) was included in the formulations, anti-microbial coatings were readily available. Titanium oxide nano particles can disinfect or clean surfaces exposed to light, thus working as a bactericidal or photooxidizing agent. This formulation can clean soiling, control or suppress bacterial proliferation, and reduce the frequency of cleaning or disinfection in the food industry, kitchens, bathrooms, washrooms, hospitals, glazing and facades.

Example 7

Removal of the Solvent

In this example, 2 g of PVB (170000~250000 g/mol, Butvar® B-72 from Solutia, Inc.) can be grounded with a Spex Freezer/mill 6770 in liquid nitrogen for 10 cycles at default configuration by the manufacturer, each cycle lasting 3 minutes. Particles of about 5 μm~about 100 μm are generated. To these particles, a solution of 1,3-bis(hydroxypropyl)tetramethyldisiloxane (0.4 g) in chloroform (2 ml) is introduced and mixed manually with a spatula for 2 minutes to create uniformly coated particles. Finally, the coated particles are dried under vacuum at ambient temperature for 4 hrs for use later.

The disclosure illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure claimed.

Thus, it should be understood that although the present disclosure has been specifically disclosed by preferred embodiments and optional features, modification, improvement and variation of the disclosure embodied therein herein disclosed may be resorted to by those skilled in the art, and that such modifications, improvements and variations are considered to be within the scope of this disclosure. The materials, methods, and examples provided here are representative of preferred embodiments, are exemplary, and are not intended as limitations on the scope of the disclosure.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein.

In addition, where features or aspects of the disclosure are described in terms of Markush groups, those skilled in the art will recognize that the disclosure is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

What is claimed is:

1. A composition comprising polyvinyl acetal (PVA) and siloxane, wherein the siloxane comprises a hydrophilic group, and wherein the PVA has a structure of:

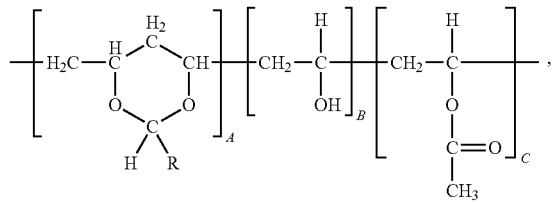

wherein R is selected from the group of methyl, ethyl, propyl, butyl, hexyl or benzyl, A is an integer in the range of from about 50 to about 1800, B is an integer in the range of from about 10 to about 800 and C is an integer from the range of from about 0 to about 1000, and wherein the butyl constitutes about 70% to about 90% of R.

2. The composition of claim 1, further comprising a solvent.

3. The composition of claim 1, wherein the hydrophilic group comprises one or more of the group of halogen, oxygen, nitrogen, sulfur or phosphorus.

4. The composition of claim 1, wherein the hydrophilic group is one or more of the group of a carboxylic acid, an amino group, a hydroxyl group, an epoxy group or an anhydride group.

5. The composition of claim 4, wherein the hydrophilic group is selected from the group of:
    (3-glycidoxypropyl)dimethylethoxysilane,
    (3-glycidoxypropyl)pentamethyldisiloxane,
    (3-glycidoxypropyl)methyldiethoxysilane,
    (3-glycidoxypropyl)triethoxysilane,
    5,6-epoxyhexyltriethoxysilane, (3-glycidoxypropyl)bis(trimethylsiloxy)methylsilane,
1,3-bis(glycidoxypropyl)tetramethyldisiloxane,
1,5-bis(glycidoxypropyl)-3-phenyl-1,1,3,5,5-pentamethyltrisiloxane,
bis[2-(3,4-epoxycyclohexyl)ethyl]tetramethyldisiloxane,
mono-(2,3-epoxy)propylether terminated polydimethylsiloxane,
epoxypropoxypropyl terminated polydimethylsiloxane,
epoxycyclohexylethyl terminated polydimethylsiloxane,
epoxypropylheptaisobutyl-T8-silsesquioxane,
succinic anhydride terminated polydimethylsiloxane,
bis(2-hydroxyethyl)-3-aminopropyltriethoxysilane,
1,3-bis(hydroxypropyl)tetramethyldisiloxane,
1,3-bis(hydroxybutyl)tetramethyldisiloxane,
monocarbinol terminated polydimethylsiloxane,
3-[hydroxy(polyethyleneoxy)propyl]heptamethyltrisiloxane,
trimethylsilylpropionic acid,
1,3-bis(3-carboxypropyl)tetramethyldisiloxane, or
3-(triethoxysilyl)propylsuccinic anhydride.

6. The composition of claim 1, wherein the siloxane has a structure of:

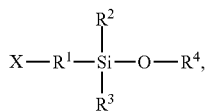

wherein:
X is selected from the group consisting of an amino group, an epoxy group, a hydroxyl group, a carboxylic acid group, and a maleic anhydride group;
R$^1$ is a divalent organic group optionally substituted with an oxygen, nitrogen, or sulfur atom, or is selected from the group consisting of a substituted or non-substituted C$_2$-C$_{20}$-aliphatic group, a substituted or non-substituted aromatic group, and a substituted or non-substituted aliphatic aromatic group;
R$^2$ and R$^3$ are independently selected from the group consisting of a lower alkyl group, a lower alkoxy group, and a polymeric siloxane group;
R$^4$ is selected from the group consisting of a lower alkyl group, a polymeric siloxane group and

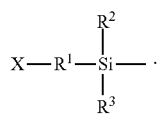

7. The composition of claim 1, wherein the PVA has a molecular weight from about 25,000 to about 250,000.
8. The composition of claim 1, wherein the PVA has a degree of polymerization of from about 200 to about 2,000.
9. The composition of claim 1, wherein the degree of polymerization is from about 400 to about 800.
10. The composition of claim 1, wherein the PVA has a degree of hydrolysis greater than about 80 mol %.
11. The composition of claim 10, wherein the degree of hydrolysis is greater than about 90 mol %.
12. The composition of claim 1, wherein the PVA has a concentration of from about 0.1 wt/vol % to about 60 wt/vol % in the composition.

13. The composition of claim 12, wherein the PVA has a concentration of from about 1 wt/vol % to about 30 wt/vol % in the composition.
14. The composition of claim 2, wherein the solvent comprises an inorganic solvent.
15. The composition of claim 14, wherein the inorganic solvent is water, saline or combinations thereof.
16. The composition of claim 2, wherein the solvent comprises an organic solvent.
17. The composition of claim 16, wherein the organic solvent is one or more of the group of methanol, ethanol, isopropanol, n-propanol, butanol, methyl cellosolve, butyl cellosolve, methyl acetate, ethyl acetate, isopropyl acetate, butyl acetate, acetone, methyl ethyl ketone, toluene, xylene, dichloromethane or chloroform.
18. The composition of claim 1, further comprising an antimicrobial agent.
19. The composition of claim 18, wherein the antimicrobial agent is one or more of the group of silver compounds, quaternary ammonium cations, or acid-anionic surfactants.
20. The composition of claim 1, further comprising a pigment.
21. The composition of claim 20, wherein the pigment is one or more of the group of iron oxides, titanium dioxides, extender pigments ultramarine pigments, manganese violet, mixed metal oxide pigments, fluorescent pigments, carbon black, magnetite, lodestone, or magnetic iron oxide.
22. The composition of claim 1, further comprising an anti-inflammatory agent.
23. The composition of claim 22, wherein the anti-inflammatory agent is one or more of the group of ibuprofen, naproxen sodium, aspirin, ketoprofen, procaine, cocaine, lidocaine, prilocaine, bupivacaine, levobupivacaine, ropivacaine or dibucaine.
24. The composition of claim 1, further comprising an anesthetic agent.
25. The composition of claim 24, wherein the anesthetic agent is one or more of the group of lidocaine, prilocaine, bupivicaine, levobupivacaine, ropivacaine, mepivacaine or dibucaine.
26. The composition of claim 1, further comprising a hemostatic agent.
27. The composition of claim 26, wherein the hemostatic agent is one or more of the group of oxidized regenerated cellulose, gelatin, fibrin, thrombin, alginate, zeolite, collagen or chitosan.
28. The composition of claim 1 provided in a gel form.
29. The composition of claim 1 provided in a liquid form.
30. The composition of claim 1, wherein the composition is pharmaceutically acceptable.
31. A composition prepared by admixing PVA and siloxane, wherein the siloxane comprises a hydrophilic group, and wherein the PVA has a structure of:

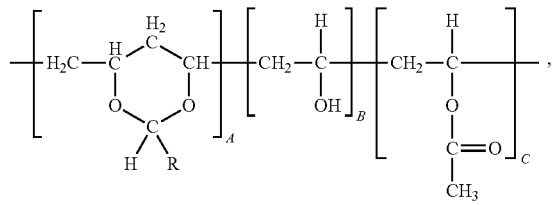

wherein R is selected from the group of methyl, ethyl, propyl, butyl, hexyl or benzyl, A is an integer in the range of from about 50 to about 1800, B is an integer in the range of from about 10 to about 800 and C is an integer from the range of from about 0 to about 1000, and wherein the butyl constitutes about 70% to about 90% of R.

32. The composition of claim 31, further comprising admixing the PVA and/or siloxane with a solvent.

33. A film that is obtained by reducing the content of the solvent in a composition of claim 1.

34. A film that is obtainable by reducing the content of the solvent in a composition of claim 1.

35. The film of claim 33, wherein the solvent is reduced by evaporation.

36. A kit comprising, in two or more separate compartments, polyvinyl acetal (PVA) and siloxane, wherein the siloxane comprises a hydrophilic group, and wherein the PVA has a structure of:

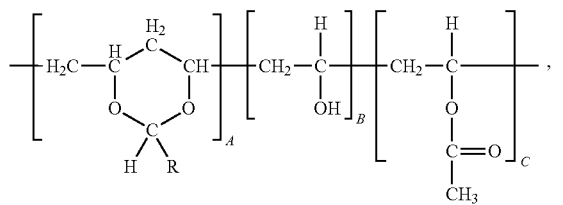

wherein R is selected from the group of methyl, ethyl, propyl, butyl, hexyl or benzyl, A is an integer in the range of from about 50 to about 1800, B is an integer in the range of from about 10 to about 800 and C is an integer from the range of from about 0 to about 1000, and wherein the butyl constitutes about 70% to about 90% of R.

37. The kit of claim 36, further comprising a solvent.

38. The kit of claim 36, further comprising one or more of an antimicrobial agent, a pigment, an anti-inflammatory agent, an anesthetic agent or a hemostatic agent.

39. A method of preparing a film on a skin, comprising applying a suitable amount of a composition of claim 1 on the skin and allowing the solvent to evaporate.

40. A method of preparing an antimicrobial sealant on a skin, comprising applying a suitable amount of a composition of claim 18 on the skin and allowing the solvent to evaporate.

41. A method of preparing a body paint on a skin, comprising applying a suitable amount of a composition of claim 20 on the skin and allowing the solvent to evaporate.

42. A method of preparing a composition of claim 1, comprising admixing polyvinyl acetal (PVA) and siloxane, wherein the siloxane comprises a hydrophilic group.

43. The method of claim 42, further comprising admixing a solvent to the composition followed by removing the solvent from the composition.

* * * * *